United States Patent [19]

Robinson

[11] Patent Number: 5,476,097

[45] Date of Patent: Dec. 19, 1995

[54] SIMULTANEOUS ULTRASONIC IMAGING AND DOPPLER DISPLAY SYSTEM

[75] Inventor: Marshall T. Robinson, Snohomish, Wash.

[73] Assignee: Advanced Technology Laboratories, Inc., Bothell, Wash.

[21] Appl. No.: 322,802

[22] Filed: Oct. 13, 1994

[51] Int. Cl.[6] ........................................................ A61B 8/06
[52] U.S. Cl. ...................................................... 128/660.05
[58] Field of Search ........................ 128/660.04–660.05, 128/661.08–661.10; 73/861.25

[56] References Cited

U.S. PATENT DOCUMENTS

| | | | |
|---|---|---|---|
| 4,559,952 | 12/1985 | Angelsen et al. | 73/861.25 X |
| 4,817,617 | 4/1989 | Takeuchi et al. | 128/661.09 X |
| 4,848,354 | 7/1989 | Angelsen et al. | 128/660.05 |
| 4,934,373 | 6/1990 | Angelsen et al. | 128/661.09 |
| 5,016,641 | 5/1991 | Schwartz | 128/661.09 |
| 5,078,146 | 1/1992 | Sato | 128/661.08 |
| 5,083,566 | 1/1992 | Baba | 128/660.05 |
| 5,188,113 | 2/1993 | Sato et al. | 128/660.05 X |
| 5,220,923 | 6/1993 | Hagiwara et al. | 128/661.09 |
| 5,301,670 | 4/1994 | Sato et al. | 128/660.05 |

*Primary Examiner*—Francis Jaworski
*Attorney, Agent, or Firm*—W. Brinton Yorks, Jr.

[57] ABSTRACT

An ultrasonic diagnostic imaging system is provided by which an ultrasonic image and Doppler flow information are simultaneously displayed from echo acquisition sequences alternating between image signal acquisition and Doppler signal acquisition. To continuously display Doppler information during the intervals that images signal acquisition is occurring, these gaps in Doppler signal acquisition are filled by signals derived from the Doppler signals received prior to and succeeding the gaps. The Doppler signals received prior to the gap are used to produce spectrally continuous signals extending over the initial portion of the gap. The Doppler signals received following the gap are used to produce spectrally continuous signals extending over the final portion of the gap. A gapsize calculator is responsive to variations in system scanning parameters to set the durations of the successive image and Doppler signal acquisition intervals to obtain optimal frame rates of display.

13 Claims, 5 Drawing Sheets

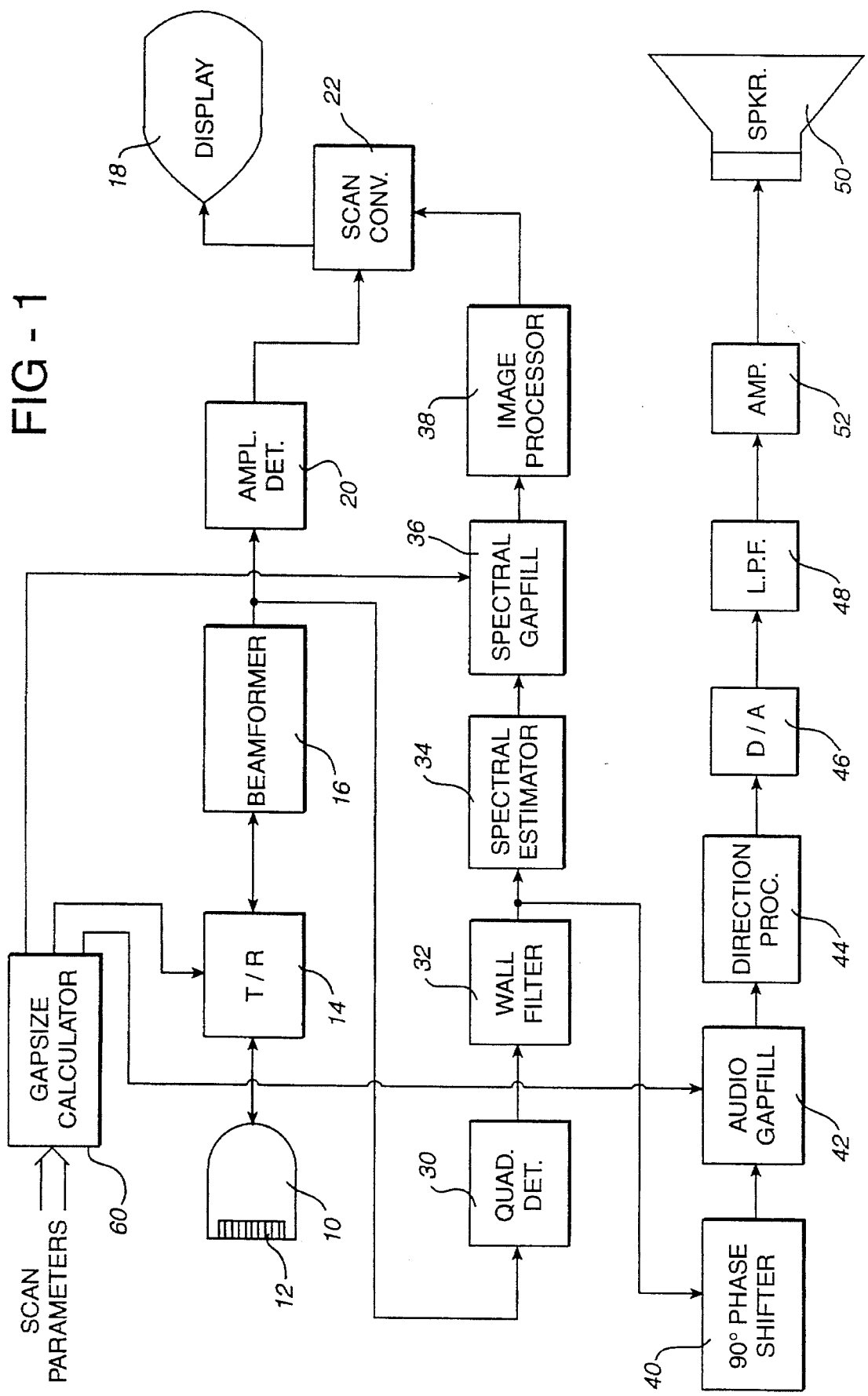

SIMULTANEOUS ULTRASONIC IMAGING AND DOPPLER DISPLAY SYSTEM

This invention relates to improvements in ultrasonic diagnostic imaging techniques, and in particular to ultrasonic imaging systems which simultaneously acquire and display a two dimensional image and Doppler flow information.

When performing real time ultrasonic diagnostic imaging it is desirable to acquire and display new information from within a patient's body as rapidly as possible. The information in a real time imaging system is updated by the acquisition and display of new frames of information. Hence the rapidity of the frame rate is a governing factor on the diagnostic utility and appearance of a real time ultrasonic image display.

A new display frame is assembled by an ultrasound system by scanning a subject area of a patient with ultrasound beams transmitted in a plurality of directions over the subject area. The sequence of echoes returning from each direction from the shallowest to the deepest depth of scan is referred to as a line. A plurality of such lines are spatially arranged side by side for display as a two dimensional image of the subject area of the patient's body. The faster the lines can be acquired and assembled in an image frame, the higher the frame rate of display. The time required to acquire and assemble the image frame is dependent upon the processing speed of the ultrasound system, and unvarying physical principles such as the speed of travel of ultrasonic waves through the tissue of the body.

The frame rate of display can be dramatically reduced when multiple types of information are being displayed simultaneously. For instance, it is frequently desirable to simultaneously display Doppler information concerning the flow state in the patient's body together with a two dimensional image of the region of the body in which the flow is occurring. This requires the acquisition of lines of image information for two dimensional display, and also lines from which Doppler information can be extracted. The time required to assemble an image frame is thus dependent upon the time required to acquire, process and assemble the image lines, and also the additional time required to acquire, process and assemble Doppler information for display.

It is generally desirable to use different scanning techniques for two dimensional images and Doppler information. The duration and bandwidths of the scanning beam pulses and Doppler pulses are generally chosen to be distinctly different, for instance. During the time of pulse transmission and reception of Doppler echoes, for instance, there is no new information being acquired for two dimensional imaging. Correspondingly there is no acquisition of Doppler information while two dimensional image lines are being acquired. Doppler and image lines must be acquired in some form of time interleaved sequence.

This need for time interleaved sequencing of Doppler and image scanning creates a problem in the display of the Doppler information, as some of the forms of Doppler display are essentially time continuous. For example, the received Doppler signal is often reproduced as a continuous audible signal which cannot be interrupted during the acquisition of two dimensional image lines. Flow velocity information can also be displayed as a continuous spectral display of high density Doppler information. Interruption of this continuous display is also undesirable. To accommodate such continuous audible and visual displays ultrasound processing systems can incorporate techniques for producing estimated display signals during the times that Doppler reception is interrupted for image acquisition. U.S. Pat. No. 5,016,641 (Schwartz) shows one approach for filling these gaps in time when Doppler information is not being acquired. In that patent received Doppler information is used to produce a synthetic Doppler spectrum during the times that imaging is being performed, and the gaps in the audible Doppler tone and the visual spectral display are filled by time domain signals derived from the synthetic spectrum. Other techniques have included producing filtered signals during these gaps, with the filter characteristics determined by the preceding Doppler signals, or simply filling the gaps by repeating previously received Doppler information during the times that imaging is being performed. These techniques can lead to distortion and other artifacts as the gaps between Doppler acquisition periods become extended, resulting in efforts to minimize the gap duration to as great a degree as possible. But the minimization of the gap durations reduces the time available to perform image acquisition, extending the time needed to acquire a full image and hence the time required to assemble a full image frame. The image frame rate deteriorates accordingly.

In accordance with the principles of the present invention an ultrasonic diagnostic imaging system is provided which simultaneously acquires and displays a two dimensional image and Doppler flow information. Scanning is performed by acquiring lines of two dimensional image information and Doppler information in a time interleaved manner. During the gaps in time that Doppler information is not being acquired the system utilizes Doppler information acquired prior to and following the time gap to span the gap time. The Doppler information acquired prior to the gap time is used to fill a first portion of the gap starting at the time when the gap began, and the Doppler information acquired after the end of the gap is used to fill a second portion of the gap extending backward from the end of the gap to the end of the first portion. This gapfilling technique provides more continuous spectral and audio continuity with each end of the gap, permitting larger gaps to be filled without generating objectionable distortion or artifacts. This greater flexibility in time interleaved scanning can be used in conjunction with an optimization of the interleaved periods of Doppler and image scanning based upon a variety of scan parameters. With larger gaps available for the acquisition of two dimensional image lines, higher image frame rates can be maintained while performing simultaneous two dimensional and Doppler imaging.

In the drawings:

FIG. 1 is a block diagram of an ultrasonic diagnostic imaging system constructed in accordance with the present invention;

Figure 2A:
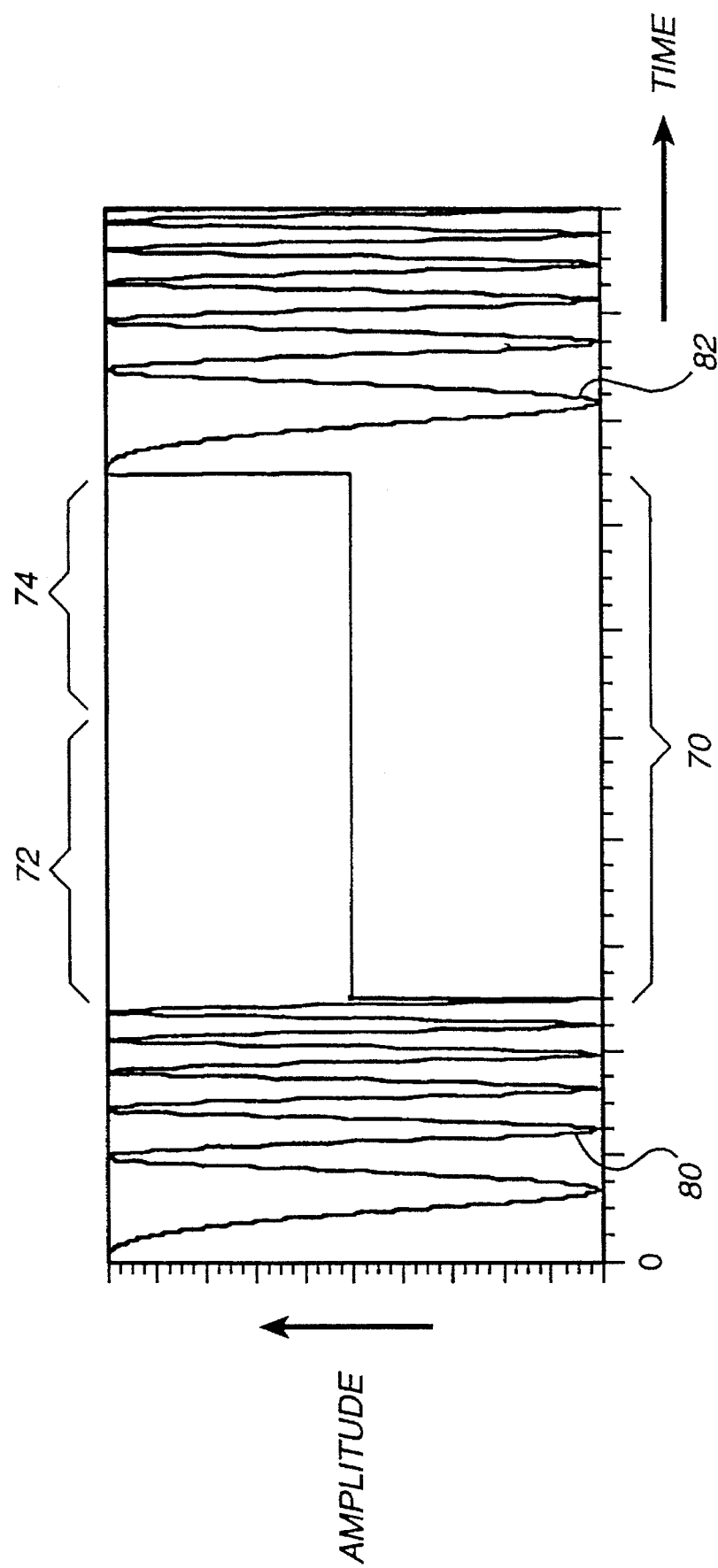
FIGS. 2a and 2b illustrate the filling of an audio spectrum gap in accordance with the principles of the present invention.

Referring first to FIG. 1 a block diagram of an ultrasonic diagnostic imaging system constructed in accordance with the principles of the present invention is shown. A scanhead 10 includes a multielement transducer array 12 for scanning a patient with beams of ultrasonic energy and receiving returning echoes. The scanhead 10 is switched between the modes of transmission and reception by a transmitter/receiver 14. The focusing and steering of the transmitted ultrasonic beam and the focusing and spatial beamforming of the received echo signals is performed by a beamformer 16.

The lines of echo signals produced by the beamformer are applied to two detectors for the two types of information being processed. An amplitude detector 20 performs amplitude detection of lines of echo information which are to be used in a two dimensional image. The detected lines are provided to a scan converter 22 which arranges the lines in a desired spatial display format, such as a sector or rectangular image. The scan converter may also provide further processing enhancements of the image, such as interpolating additional spatial lines between the locations of the received lines or enhancing the contrast within the image. The image may be displayed as a two dimensional image plane, or a plurality of planar image data can be processed to produce a three dimensional image.

A quadrature detector 30 performs quadrature detection of lines of echo information which are to be used for Doppler processing and display. The quadrature detector produces Doppler samples in an I,Q format. The I,Q samples are filtered by a wall filter 32 to remove low frequency clutter from the Doppler information. The filtered Doppler information signals are then provided to a visual display processing subsystem and an audio display processing subsystem.

The visual display processing subsystem produces a visual spectral display and begins with a spectral estimation processor 34 which estimates the Doppler shift frequency at particular points in time from a number of lines of Doppler information signals. The spectral display also relates to a particular location in a patient's body called the sample volume. The spectral display shows the frequency spectrum of flow at the sample volume location, which relates directly to flow velocity. The spectral estimation processor will produce a continuous sequence of Doppler frequency estimations while it is being provided with a stream of new Doppler signals, but will cease producing valid estimates when the Doppler signals are interrupted to produce lines for image display. The spectral estimation processor 34 resumes the production of updated frequency estimates when the acquisition of Doppler echo information resumes.

Figure 4:
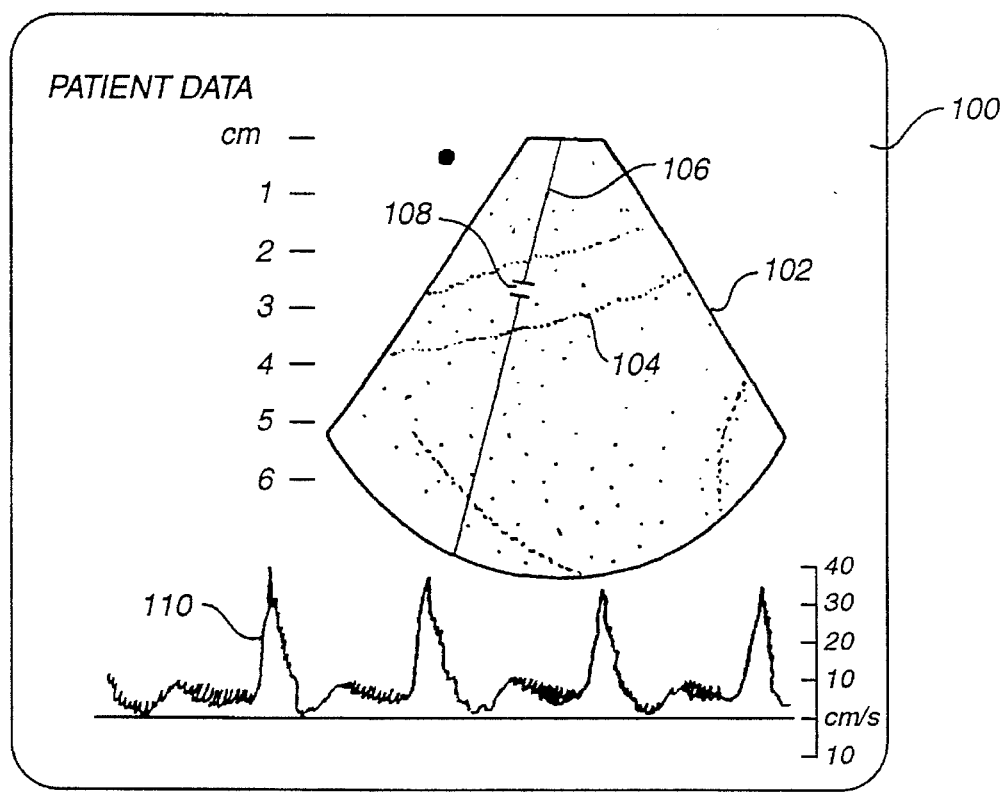
FIG. 4 illustrates a simultaneous two dimensional image and spectral Doppler display.

The Doppler frequency estimates are provided to a spectral gapfill processor 36 which develops spectral display samples to be used during the gaps when the spectral estimation processor is not providing valid Doppler information. The samples developed by the spectral gapfill processor to fill the gaps are produced as described below. The continuous stream of received and gapfilled Doppler samples are provided to an image processor 38, which produces a spectral Doppler display of the desired format. The spectral Doppler display is provided to the scan converter where it is combined for display with the two dimensional image in a single display frame. Successive frames are displayed on the video display 18 and appear as shown in FIG. 4. This figure shows a displayed frame 100 which includes the simultaneous display of a two dimensional image 102 and a spectral Doppler waveform 110.

The wall filtered Doppler information signals are also provided to an audio display processing subsystem which begins with a 90° phase shifter 40. The phase shift imparted to the Doppler signals by this phase shifter enables the processing chain to distinguish between flow velocities in opposite directions. An audio gapfill processor 42 processes the received Doppler signals to fill the periods of time between the acquisition of Doppler information with synthesized signal information as described below. The continuous stream of received and gapfilled signals is applied to a direction processor 44 which converts the signals into signals representative of forward and reverse directions of flow. The processed signals, now in an audio spectrum, are converted to an analog wave by a digital to analog converter 46. The analog wave is filtered by a low pass filter 48 to filter out high frequency artifacts and the filtered wave is amplified by an amplifier 52. The amplified audio wave is reproduced as a Doppler tone by a loudspeaker 50.

Figure 2B:
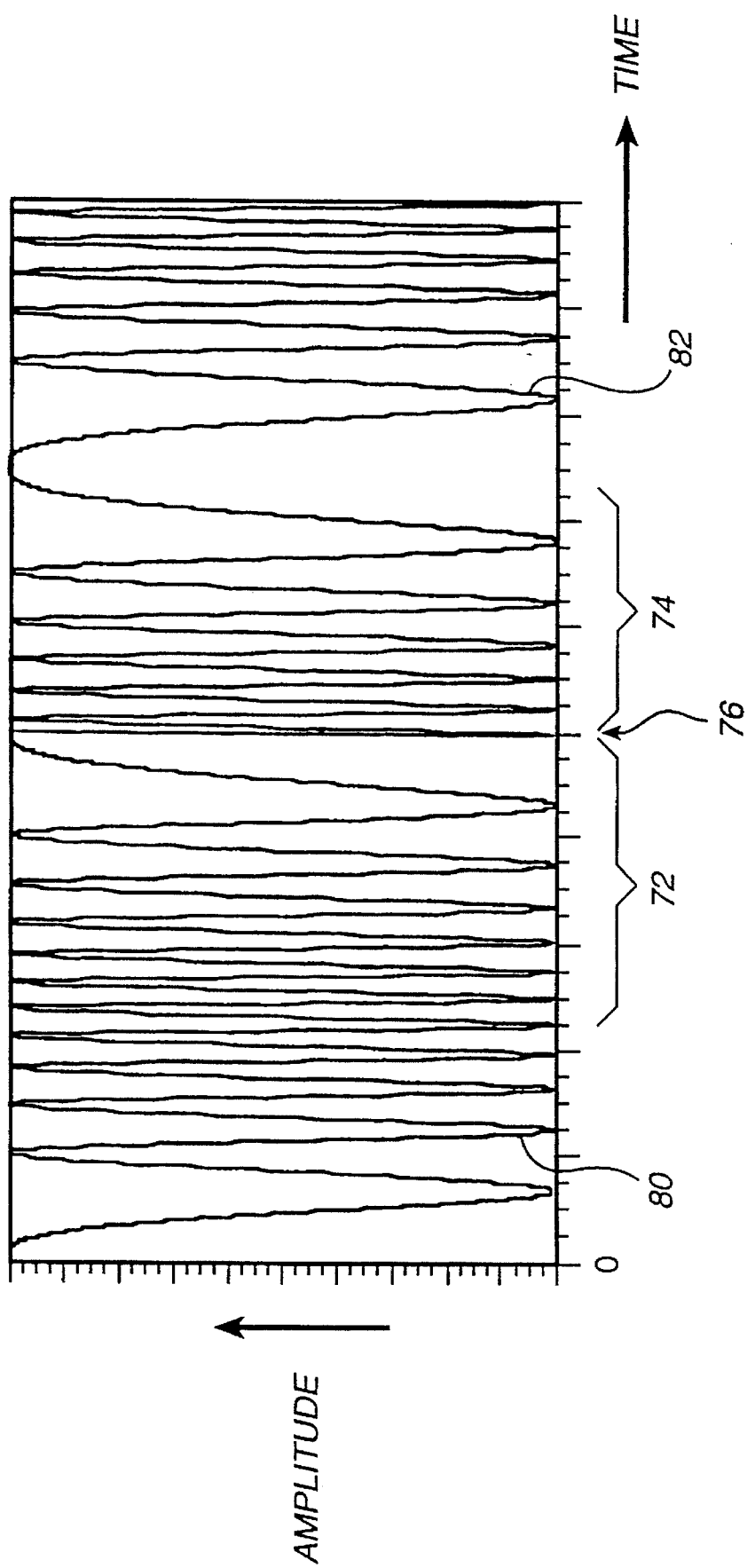

Referring to FIGS. 2a and 2b, the signal processing performed by the audio gapfill processor 42 is shown. FIG. 2a shows at the left an audio wave 80 formed by a succession of digital signal samples which ends at the beginning of a gap 70 in time during which no new Doppler information is received while the ultrasound system acquires lines of image information. At the end of the gap 70 an audio wave 82 resumes with the commencement of reception of new Doppler information as the ultrasound system returns to Doppler scanning.

The audio gapfill processor 42 stores the signal samples preceding and following the gap 70 and identifies the duration of the gap. Alternatively the processor 42 can be informed of the duration of the gap by a gapsize calculator which will be discussed below. Based upon the knowledge of the gap size the processor 42 begins filling the gap from each end of the gap with samples drawn from respective sides of the gap. In the case of the initial portion 72 of the gap, the processor 42 begins filling the gap from left to right (forward in time) with samples taken from the time of commencement of the gap and proceeding from right to left (backward in time). The last signal sample immediately preceding the gap portion 72 is used as the next sample in time, the first gapfilling sample. The signal sample which precedes the last signal sample before the gap is used as the second gapfilling sample, and so forth. As a result of this technique the initial portion 72 of the gap in the audio wave is filled with a spectrum which is a continuation of the spectrum of the received signal 80 at the beginning of the gap 70 and in a reverse time sequence from the spectral progression leading up to the beginning of the gap.

The same technique, but in a reverse time order, is used to fill the latter portion 74 of the gap 70. The first received sample after the gap 70 is used as the gapfilling sample adjacent to the end of the gap. The second received sample after the gap is used as the gapfilling sample preceding (in sequence and in time) the last gapfilling sample, and so forth. Thus, the latter portion 74 of the gap in the audio wave is filled with a spectrum which is a continuation of the spectrum of the received signal following the gap 70 and in a reverse time sequence from the spectral progression of the received signal which follows the gap.

Thus it is seen that each portion of the gap is filled with gapfilling signals that smoothly progress spectrally from the signal spectrum at the beginning and ending points of the gap, as shown in FIG. 2b. However, a spectral discontinuity is likely to exist in the middle of the gap 76 where the gapfilling samples proceeding from the two edges of the gap come together. While this discontinuity could be smoothed by averaging or interpolating the gapfilling samples as they approach each other at the gap center, it has been found sufficient to eliminate artifacts of this discontinuity by the cutoff of the low pass filter 48.

This inventive technique of smoothly continuing the spectral characteristics of the received signal information on each side of the gap has been found to enable the use and filling of relatively lengthy gaps in Doppler signal acquisition without the appearance of annoying clicks or distortion in the Doppler audio signal. Consequently, gapfilling in accordance with the inventive technique facilitates the ability to acquire frames of image information in a shorter duration of time and hence maintain a relatively high frame rate of display.

The signal processing performed by the spectral gapfill processor 36 is explained with reference to FIGS. 3a and 3b. These figures show a portion of an exemplary spectral display which depicts the spread in flow velocities at a series of discrete points in time and their variation with time. The figures are premised upon a ramp input signal of changing velocity and would typically result from a few hundred sequential velocity estimations by the spectral estimation processor 34.

Figure 3A:
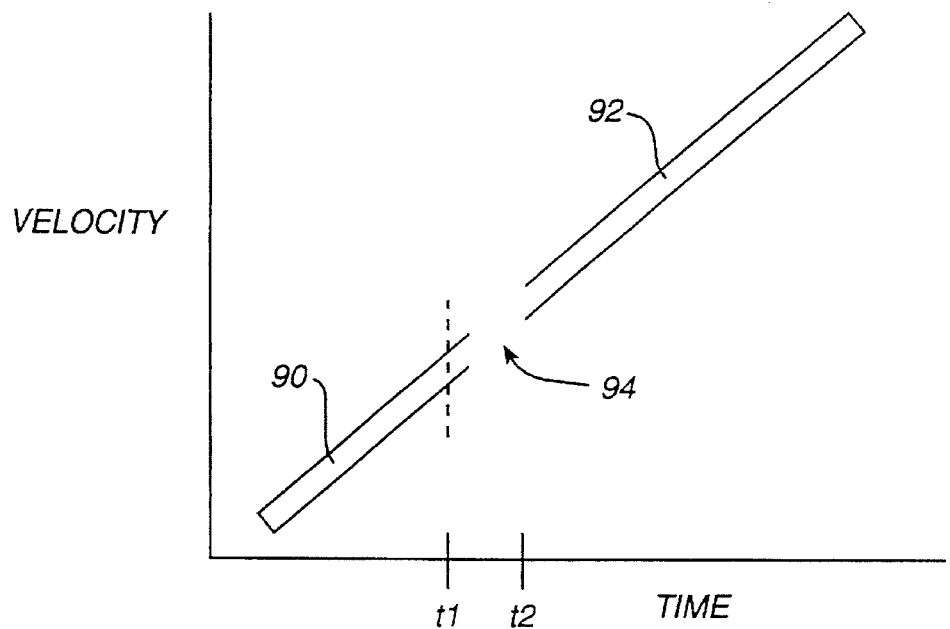
FIGS. 3a and 3b illustrate the filling of a Doppler video spectral gap in accordance with the principles of the present invention.

In FIG. 3a a spectral display comprises two sections 90, 92 of received spectral information which have been interrupted by a gap in time 94 during which image scanning is performed by the ultrasound system. In a manner similar to that of the audio gapfill processor 42, the spectral gapfill processor uses the received information 90, 92 before and after the gap 94 to develop gapfilling spectral lines proceeding toward the center of the gap from each end of the gap.

Figure 3B:
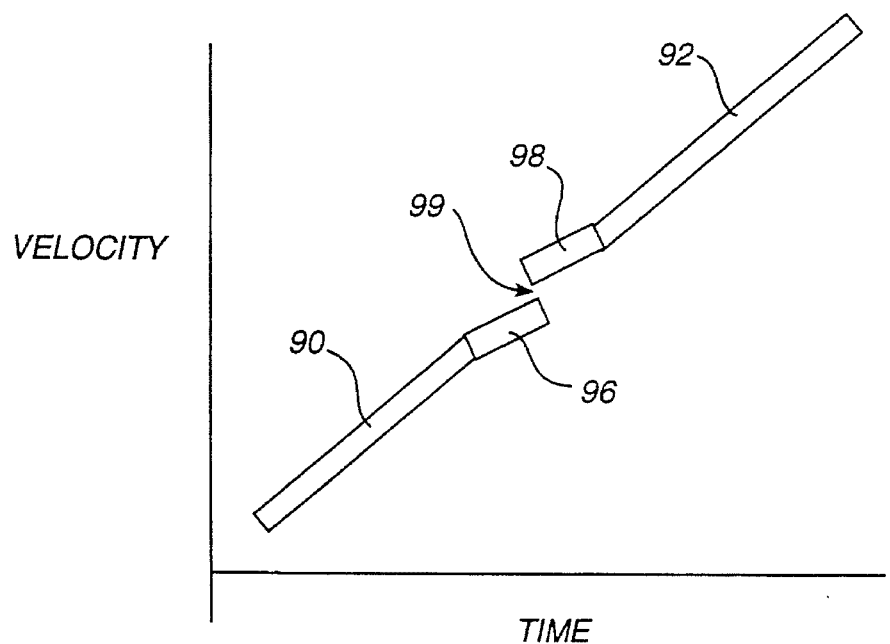

In the case of the initial portion 96 of the gap illustrated in FIG. 3b, the processor 36 begins by identifying the received spectral information existing at a time $t_1$ which precedes the beginning of the gap 94 by approximately one half of the duration of the gap. The spectral signal sample existing at time $t_1$ is displayed not once, but twice in succession. Likewise, the spectral information sample next produced by the spectral estimation processor is reproduced twice for display. This doubling of the use of the received spectral estimates for display effectively stretches their use over a time which is twice that over which they were received, thus stretching the received samples over half of the gap 94 and in a manner which provides smooth spectral continuity.

It may be appreciated that spectral samples can be repeated two, three, or more times so as to fill the initial portion of the gap. When the valid spectral samples are repeated higher multiple times, the initial repeated sample will be closer to the beginning of the gap than time $t_1$ in the preceding example.

Following the gap 94 the latter portion 98 of the gap 94 is filled by similarly repeating spectral signal samples, but this time using samples of the section 92 received subsequent to the gap. In the illusrated example the first valid spectral signal sample received after the gap at time $t_2$ is displayed as a gapfilling sample near the center 99 of the gap and is repeated. The second valid spectral signal sample follows and is repeated, and the succession of repeating samples continues until the sequence merges with the normally spaced real time sequence 92 and the repeating of samples is ended. Again, spectral continuity is provided over the latter portion 98 of the gap and extending forward in time through the end of the gap and into the valid sample sequence 92.

As was the case of the audio gapfilling technique, this technique results in the ability to fill greater duration gaps in the video display spectrum before artifacts such as dots become visible at the center of the gap where a spectral discontinuity is likely to exist. Even greater duration gaps could be employed for even higher video frame rates by smoothing the discontinuities through averaging, interpolating or filtering the gapfilling samples in the center of the gap. An example of the spectral display which is improved by the inventive gapfilling technique is shown at 110 in FIG. 4. FIG. 4 also shows the simultaneously produced two dimensional image 102. The image 102 shows the structure of a blood vessel 104, the directional line 106 along which Doppler information is acquired, and the sample volume 108 positioned in the blood vessel 104 which is the source of the signals used to produce the Doppler spectrum display 110.

Figure 5:
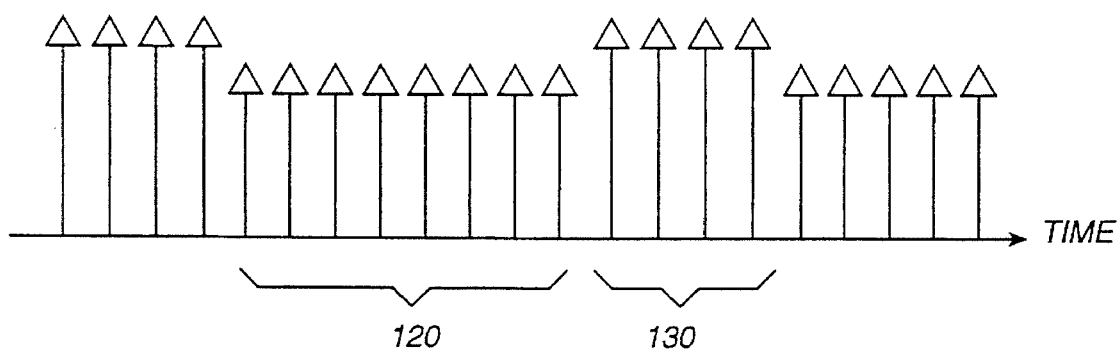
FIG. 5 illustrates the variable relationship between periods of Doppler and two dimensional scanning made possible by the improvements provided by the present invention.

Due to the fact that the inventive gapfilling technique makes possible the use of relative large gaps between intervals of Doppler signal acquisition without the onset of visual artifacts or audible distortion, it is possible to optimally proportion the interleaved image scanning and Doppler signal acquisition intervals for higher frame rates. This is done by a gapsize calculator 60 shown in FIG. 1. The gapsize calculator receives as inputs the values of a number of user variable scan parameters and based upon the magnitudes and changes in these parameters adjusts the relative proportions of the image scan and Doppler acquisition intervals and their respective durations for optimally high frame rates. Once these interleaved intervals have been calculated by the gapsize calculator, the transmitter/receiver 14 is controlled to transmit either image scan pulses or Doppler scan pulses as appropriate, and the processors for the received signals such as the spectral gapfill processor 36 and the audio gapfill processor 42 are conditioned for reception and processing of the resulting sequence. FIG. 5 for instance shows a number of vertical arrows, each representing the time of pulse transmission for either imaging or Doppler. The taller arrows represent Doppler pulse transmissions and the shorter arrows represent imaging pulse transmissions. The figure shows a first interval 120 during which a sequence of eight successive image lines are acquired, followed by a second interval 130 during which a sequence of four successive Doppler lines are acquired. The effect of the gapsize calculator 60 is to change the relative lengths of these two intervals and their durations in response to user change of the system scan parameters. These changes could range from a situation where every image line is succeeded by a series of Doppler lines, to a situation where a full frame of image lines is acquired between each interval of Doppler signal acquisition. The benefit obtained is optimization of the greatest attainable frame rate for a given set of scanning conditions.

A number of scan parameters used by the gapsize calculator 60 to change the gapsize (the imaging interval 120) and the type of change they cause, are as follows. When the depth of a scan, such as the 6 cm. depth of the image in FIG. 4, is increased, the gapsize calculator will respond by increasing the imaging interval 120. When the frame rate of display is reduced the gapsize is correspondingly increased. As additional focal zones are added to an image the gapsize increases. As the image line density is increased the gapsize is increased. In response to a decrease in the width of the image sector the gapsize is decreased. When a zoom function is employed to enlarge a section of a full image, the gapsize is decreased. When the Doppler pulse transmission rate or PRF is decreased the gapsize is increased. A PRF change can be effected indirectly, for instance, by a change in the depth of the sample volume 108. A change in the performance of the wall filter 32, such as changing the filter characteristic to employ a steeper rolloff, will cause the gapsize to decrease. A change in the user setup or application, such as changing from an abdominal scan to a cardiac scan, may also result in a change in the gapsize. It will be appreciated of course that certain of these changes may be interactive and that limits in variation may be set as a matter of design choice. For instance, if the imaging depth is increased and it is attempted to increase the gapsize, a designed limitation on the gapsize increase could be encountered so as to prevent the onset of Doppler artifacts. As another example, the gapsize variation may be limited so as not to exceed the gapsize needed to acquire all of the lines for a full image. Such limitation may be employed in a particular embodiment as a matter of design choice.

What is claimed is:

1. An ultrasonic diagnostic imaging system which simultaneously displays image and Doppler information derived from alternate intervals of ultrasonic image signal acquisition and Doppler signal acquisition, including means for developing signals to be used for Doppler display during the gaps in Doppler information reception occurring by reason of performance by the system of image signal acquisition comprising:

means responsive to the reception of Doppler information signals for producing sequences of Doppler estimation signals during intervals of Doppler signal acquisition;

means responsive to said sequences of Doppler estimation signals for producing gapfilling signals for use in gaps between said Doppler estimation sequences including means responsive to Doppler estimation signals preceding a gap for deriving a first sequence of gapfilling signals over an initial portion of said gap, and means responsive to Doppler estimation signals following said gap for deriving a second sequence of gapfilling signals over a concluding portion of said gap; and means responsive to said sequences of Doppler estimation signals and said intervening first and second sequences of gapfilling signals for displaying Doppler information.

2. The ultrasonic diagnostic imaging system of claim 1, wherein said means for deriving a first sequence of gapfilling signals comprises means for developing a sequence of gapfilling signals preceding forward in time from the beginning of said gap which is derived from the sequence of Doppler estimation signals preceding backward in time from said beginning of said gap.

3. The ultrasonic diagnostic imaging system of claim 1, wherein said means for deriving a second sequence of gapfilling signals comprises means for developing a sequence of gapfilling signals preceding backward in time from the end of said gap which is derived from the sequence of Doppler estimation signals preceding forward in time from said end of said gap.

4. The ultrasonic diagnostic imaging system of claim 1, wherein said means for producing gapfilling signals comprises means for deriving a first sequence of gapfilling signals which are spectrally continuous with the spectrum of said Doppler estimation signals preceding said gap, and means for deriving a second sequence of gapfilling signals which are spectrally continuous with the spectrum of said Doppler estimation signals following said gap.

5. The ultrasonic diagnostic imaging system of claim 4, wherein said means for producing gapfilling signals further comprises means for smoothing the spectrum between said first and second sequences of gapfilling signals.

6. The ultrasonic diagnostic imaging system of claim 4, wherein said means for displaying Doppler information comprises an audio system.

7. The ultrasonic diagnostic imaging system of claim 1, wherein said means for deriving a first sequence of gapfilling signals comprises means for developing a sequence of gapfilling signals preceding forward in time from a Doppler estimation signal which precedes the beginning of said gap by repeating each Doppler estimation signal in succession through the Doppler estimation signal immediately preceding said gap.

8. The ultrasonic diagnostic imaging system of claim 7, wherein said means for deriving a second sequence of gapfilling signals comprises means for developing a sequence of gapfilling signals preceding forward in time from the center of said gap which is derived by repeating Doppler estimation signals preceding forward in time from said end of said gap.

9. The ultrasonic diagnostic imaging system of claim 8, wherein said means for producing gapfilling signals further comprises means for smoothing the spectrum between said first and second sequences of gapfilling signals.

10. The ultrasonic diagnostic imaging system of claim 8, wherein said means for displaying Doppler information comprises a Doppler spectral display system.

11. An ultrasonic diagnostic imaging system which simultaneously displays an ultrasonic image and a continuous display of spectral Doppler information derived from alternate scanning intervals of ultrasonic image signal acquisition and Doppler signal acquisition, comprising:

Doppler means responsive to the reception of Doppler information signals for producing Doppler estimation signals during intervals of Doppler signal acquisition;

imaging means responsive to the reception of image information signals for producing ultrasonic image lines during intervals of ultrasonic image signal acquisition;

means, coupled to said Doppler means and said imaging means, and responsive to user adjustment of scanning control parameters, for varying the durations of said intervals of Doppler signal acquisition and ultrasonic image signal acquisition;

a Doppler display gapfiller responsive to said Doppler means for filling gaps in said Doppler estimation signals occurring during said intervals of ultrasonic image signal acquisition in order to provide a substantially continuous sequence of spectral Doppler information signals; and means, coupled to said Doppler display gapfiller and said imaging means for simultaneously displaying a continuous display of Spectral Doppler information together with an ultrasonic image.

12. The ultrasonic diagnostic imaging system of claim 11, wherein said scanning control parameters comprise one or more of the parameters of depth of scan, frame rate, number of focal zones, image line density, image width, image zoom, Doppler pulse transmission rate, sample volume depth, and wall filter characteristic.

13. The ultrasonic diagnostic imaging system of claim 11, wherein said Doppler display gapfiller comprises means responsive to Doppler estimation signals preceding a gap for deriving a first sequence of gapfilling signals over an initial portion of said gap, and means responsive to Doppler estimation signals following said gap for deriving a second sequence of gapfilling signals over a concluding portion of said gap.

* * * * *